United States Patent [19]

Kajiyama

[11] Patent Number: 4,515,018
[45] Date of Patent: May 7, 1985

[54] GUIDE RAIL APPARATUS FOR AN OBJECT RUNNING AROUND PIPING

[75] Inventor: Sigeru Kajiyama, Hitachi, Japan

[73] Assignee: Hitachi, Ltd., Tokyo, Japan

[21] Appl. No.: 377,159

[22] Filed: May 11, 1982

[30] Foreign Application Priority Data

May 13, 1981 [JP] Japan .................................. 56-70802
Aug. 7, 1981 [JP] Japan .................................. 56-122960

[51] Int. Cl.³ .............................................. G01N 29/04
[52] U.S. Cl. ...................................................... 73/637
[58] Field of Search ..................... 73/432 B, 622, 637, 73/640

[56] References Cited

U.S. PATENT DOCUMENTS 3,921,440  11/1975  Toth ...................................... 73/622

FOREIGN PATENT DOCUMENTS 19451    2/1981  Japan ..................................... 73/637
47756    4/1981  Japan ..................................... 73/637
0819706  4/1981  U.S.S.R. ................................ 73/622

Primary Examiner—S. Clement Swisher
Assistant Examiner—Joseph W. Roskos
Attorney, Agent, or Firm—Antonelli, Terry & Wands

[57] ABSTRACT

A guide rail apparatus for guiding a running body running around a pipe having a complicated form such as an elbow. The apparatus includes a guide rail secured to the pipe in parallel with the weld line or others and a dynamically stable holder by which the guide rail is fixed.

4 Claims, 31 Drawing Figures

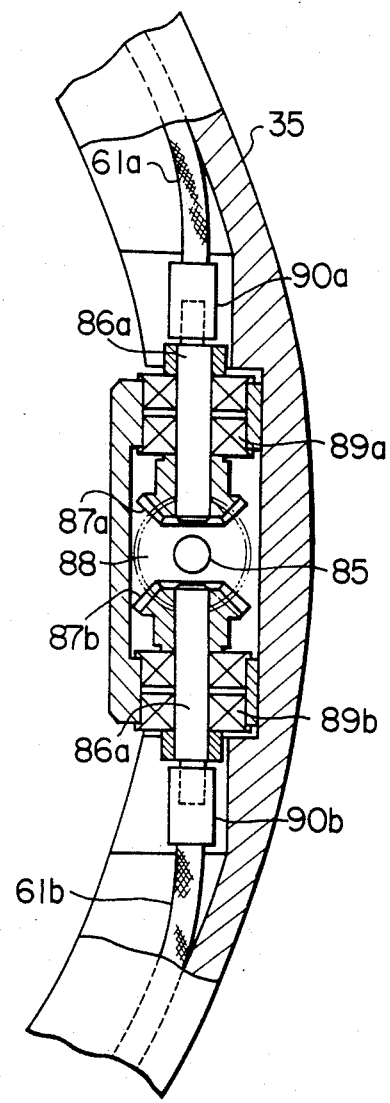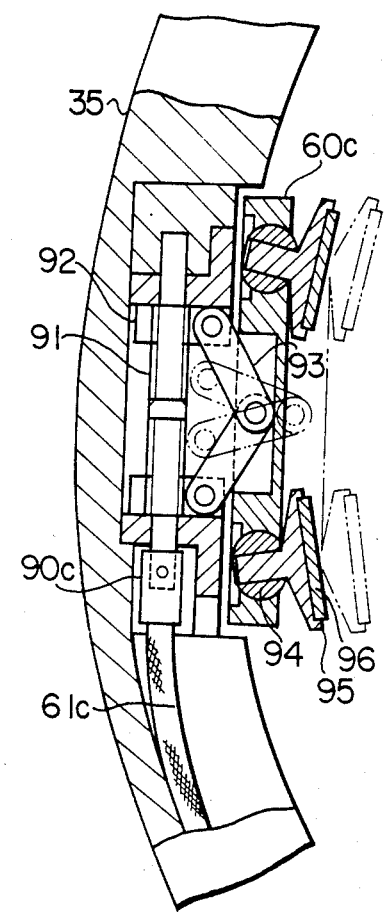

GUIDE RAIL APPARATUS FOR AN OBJECT RUNNING AROUND PIPING

BACKGROUND OF THE INVENTION

The present invention relates to a guide rail apparatus and, more particularly, to a guide rail apparatus for guiding an object around the portion of piping having complicated form such as elbow or the like. The guide rail apparatus of the invention can be applied, for example, to the guiding of running type ultrasonic flaw detector for examining weld parts of piping in unclear power station.

In plants such as nuclear power station, it is necessary to effect a periodic check of weld parts of the pressure vessel, piping and so forth for any leakage. Nondestructive inspection, particularly the ultrasonic flaw detection, is the most popular way for examining the weld parts. Hitherto, the ultrasonic flaw detection has been made mainly through manual work. Recently, however, it has been proposed to automatically and remotely control the scanning probe in order to achieve a higher efficiency. In such a method, the driving apparatus for driving the scanning probe is guided along a guide rail apparatus in the form of links previously arranged around the piping, in order to obtain correct information concerning the position of the probe. Most of the guide rail apparatus heretofore proposed, however, are designed for straight portions of the piping and, hence, can be applied only to several tens of percents of the whole portion of the piping. Namely, the weld parts of piping in nuclear power station are found mainly in the following portions; the portion where the axis is flexed, portion where the diameter of the pipe is varied, portion where an equipment is connected, and the portion where the pipe is branched or dispersed. In every part of a piping system there are portions where the axis is flexed or bent. Therefore, the rate of application of the automatic scanning system can be increased considerably by designing the guide rail apparatus for application to complicated portions of piping such as elbow.

As shown in FIG. 1, in a conventional probe driving apparatus for straight portion of the piping, a split-ring type guide rail 1 embraces the straight portion 2 of a piping in such a manner that the circumferential line of the guide rail 1 extends in parallel with the weld line 3. A driving unit 4 is mounted on the guide rail 1 by engaging rollers 5 to be able to run along the guide rail 1 in the circumferential direction so that the probe 6 scans the pipe around the weld line 3 in both circumferential and axial directions. The probe 6 is resiliently pressed against the surface to be examined by a holder 7 through a spring 8. An arm 9 carrying the holder 7 extends to the opposite side of the driving unit 4 and carries at its other end another holder 7 which presses a ball 10 resiliently against the pipe surface through another spring 8, so that the reactional force is exerted to press the probe 6 against the pipe surface due to a lever action of the arm 9. FIG. 2 shows another conventional apparatus in which a guide rail 1 is attached to the outer surface of an elbow 11 for permitting the probe 6 to scan the portion in the vicinity of the weld line 3, wherein the axial length is varied in accordance with the movement of the guide rail 1. In this known apparatus, it is necessary to vary the angle between the guide rail 1 and the arm 9 around the axis 14 of rotation and also to vary the angle between the examined surface and the arm 9. For these reasons, various difficulties are caused such as complicated manipulation, uneasy handling and troublesome processing of signals for detecting the position of the probe 6.

In Japanese Patent Application No. 92939/1978, a probe driving apparatus for an ultrasonic flaw detection of piping is proposed. However this proposed driving apparatus, however, is intended for straight pipes and operates in a manner explained hereinbelow with reference to FIG. 17. A driving unit 203 is attached to a track 207 secured to a straight pipe 201 by openable rollers 206. The driving unit 203 incorporates a motor the power of which is transmitted to a pinion 205 meshing with racks 208 formed on the track 207 so that the driving unit as a whole moves in the circumferential direction. At the same time, another motor drives a screw (not shown) extending in parallel with an arm 204 so that a holder 211, incorporating a nut meshing with the screw, is moved accompanying the arm 204. The scanning probe 202 for transmitting/receiving ultrasonic wave is made to run in both of circumferential and axial directions to thereby automatically conduct the examination. The scanning instruction is given from a remote plate by means of a cable. This apparatus, however, cannot be applied to the pipe of complicated form such as an elbow 210, because the length of the arm 204 is too large and abuts the pipe surface and because the probe 202 cannot delicately follow the examined surface of complicated form. Thus, this apparatus also fails to improve the rate of application of automatic ultrasonic flaw detection to the inspection of piping.

SUMMARY OF THE INVENTION

Accordingly, it is a primary object of the invention is to provide a guide rail apparatus for guiding an object running around piping, capable of securing moving object such as probe driving unit or the like even to pipes having no straight portion to widen the capability of attaching of the running body while improving the running stability and simplifying the signal processing and maneuverability.

To this end, the apparatus of the invention basically has a guide rail secured in parallel to a weld line of a pipe having a complicated form such as an elbow, and a dynamically stable holder fixing the guide rail. According to a preferred form of the invention, it is possible to simultaneously clamp both of the guide rail and holder by manipulation of a single haldle.

Another object of the invention is to provide a small-sized and light-weight probe driving unit capable of running smoothly and automatically following up the surface of the examination object having a complicated form such as an elbow pipe.

In order to make it possible to move the unit following up the configuration of the piping while varying the scanning stroke in accordance with the configuration, according to the invention, there is provided an expandable axial arm which is movable following up the configuration of the piping and the probe is pressed against the piping with a constant pressure following up large change in the configuration of the piping surface to widen the adaptability. Particularly, the height from the pipe surface is reduced so as to to reduce the chance of interference with peripheral structure to further increase the adaptability.

BRIEF DESCRIPTION OF THE DRAWINGS

FIG. 9 is a partly-sectioned enlarged view of a torque transmitting portion of a holder;

FIG. 10 is an enlarged partial sectional view of a movable claw;

DESCRIPTION OF THE PREFERRED EMBODIMENTS

Figure 1:
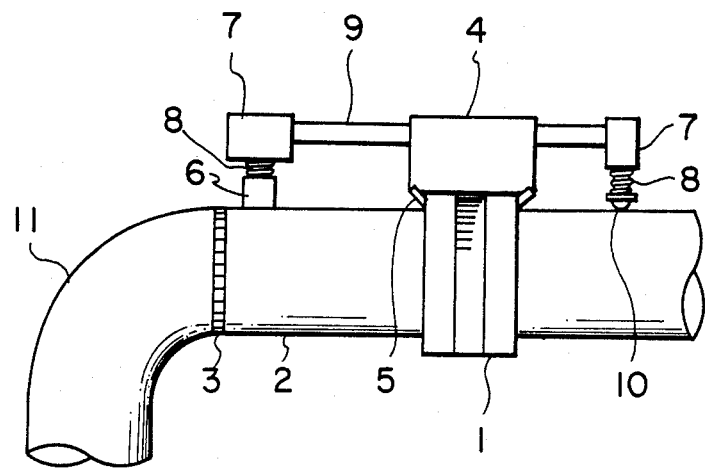
FIG. 1 is a schematic illustration of a conventional guide rail apparatus.
Figure 2:
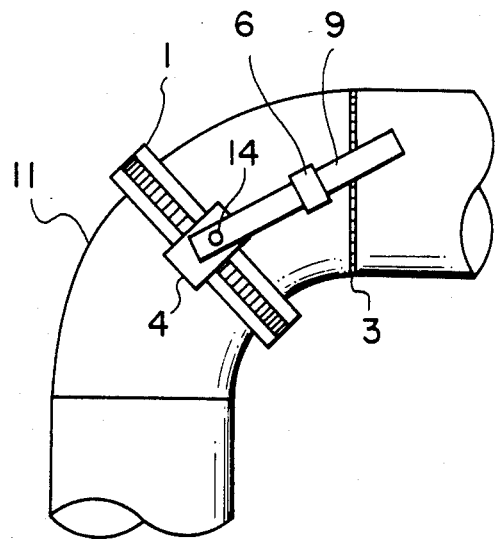
FIG. 2 is a schematic illustration of another conventional guide rail apparatus.
Figure 3:
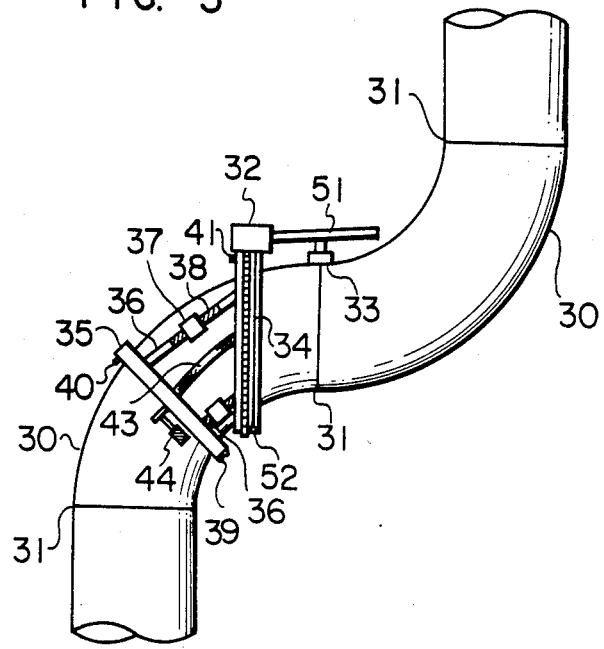
FIGS. 3 and 4 are side elevational views of an apparatus in accordance with an embodiment of the invention as viewed from different ends.
Figure 4:
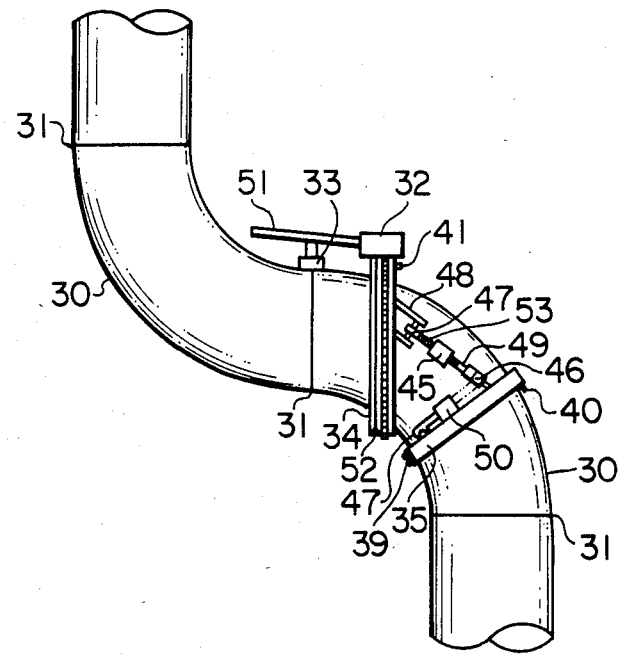

Referring now to the drawings wherein like reference numerals are used throughout the various views to designate like parts and, more particularly, to FIGS. 3 and 4, according to these figures, a guide rail apparatus according to the present invention, attached to a pair of continuous elbows bent in opposite directions, includes a guide rail designated 34 secured along a weld line 31 and fixed to the elbow by means of a holder 35 through a rib 36. The holder 35 is adapted to clamp the elbow by means of movable claws operatively related to movable claws on the guide rail 34 through a flexible shaft 43, such that the claws are pressed against the surface of the elbow by a manipulation of a handle 44. This arrangement assists the holding of the guide rail 34 by the holder 35 and enhances the total holding force including the holder 35 and the guide rail 34. The length of the rib 36 is adjustable by means of a turn buckle which includes left and right handed threaded portions 38 and a nut so that the distance between the weld line 31 and the guide rail 34 is preadjustable A driving unit 32 is attached to the guide rail 34 and is moved along the latter to make a probe 33 thereon scan the elbow in the circumferential direction. At the same time, the probe 33 is moved along the arm 51 to scan the elbow also in the axial direction.

As shown in FIG. 4, since the axes of the holder 35 and the guide rail 34 deviate from each other due to the curvature of the elbow, a rear-side rib 49 is detachably connected to the holder 48 of the guide rail 34 by means of a hook 47.

Figure 5:
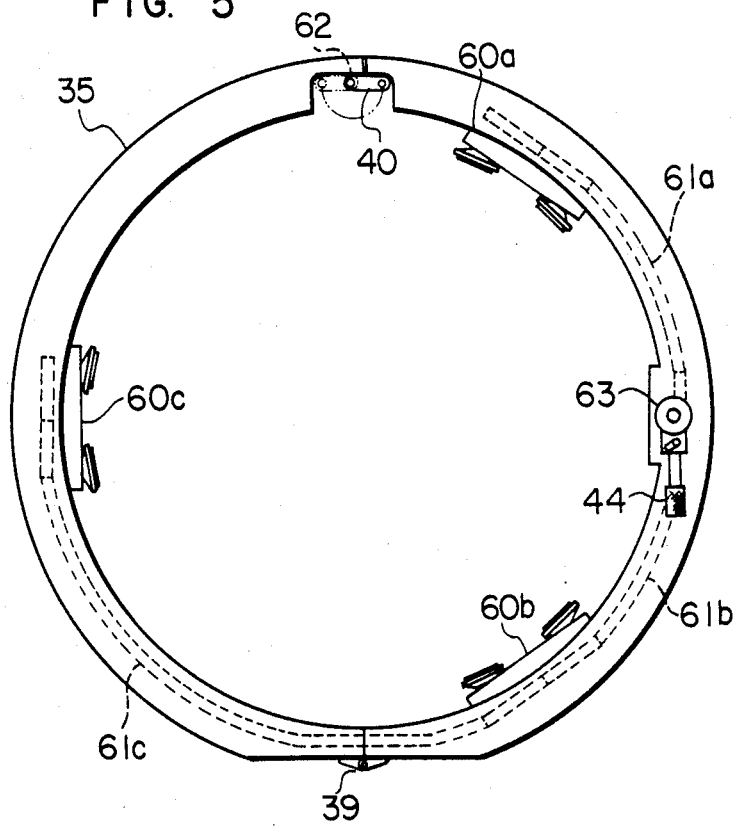
FIG. 5 is a front elevational view of a holder.
Figure 6A:
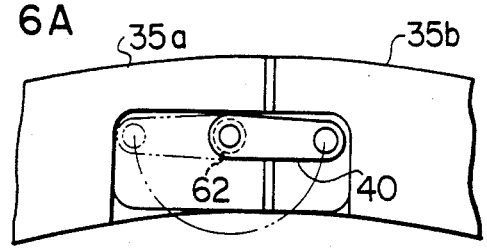
FIG. 6A is an enlarged view of a hinge portion of the holder.
Figure 6B:
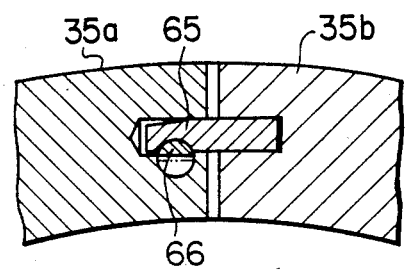
FIG. 6B is a sectional view of the central part of the hinge portion shown in FIG. 6A.

As shown in FIGS. 5, 6A and 6B, the holder 35 is formed as a split-type ring like member composed of two segments 35a, 35b hinged to each other by a hinge 39 and the two segments 35a, 35b are swingable around the hinge 39 to open and close the holder 35 for mounting on and removal from the elbow by the manipulation of a handle 40 which is rotatable around the axis of a rotary shaft 62. As the handle 40 is rotated to one position as shown by solid line, a deformed pin 66, (FIG. 6B), integral with the shaft 62, comes into an opening in a pin 65 to thereby lock the ends of the holder segments 35a, 35b. For opening the holder 35, the handle 40 is rotated to the position shown in phantom line (FIGS. 5, 6A) so that the deformed pin 66 is rotated 180° to come out of engagement with the pin 65 thereby enabling the pin 66 to be withdrawn. By so doing, it is possible to swing the holder segments 35a, 35b away from each other to form the opening for mounting on and removal of the holder 35 from the pipe.

Figure 7:
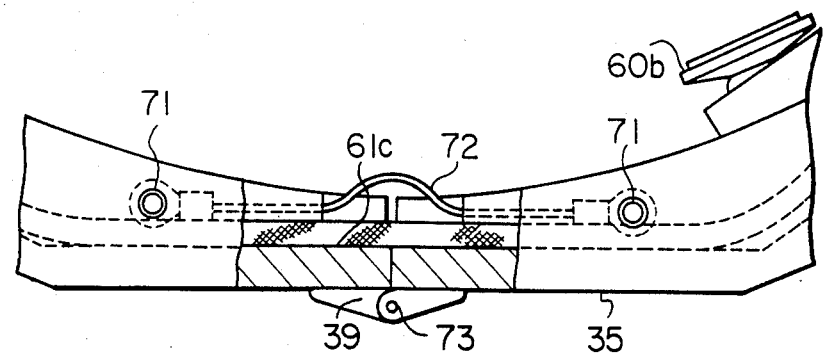
FIG. 7 is an enlarged view of the hinge portion.

As shown in FIG. 7 hinge 39 is adapted to open around a pin 73 and the opening angle thereof is limited by a wire fixed to the stationary shaft 71. On the other hand, the clamp mechanism has movable claws 60a, 60b and 60c (FIG. 5) adapted to be projected and retracted through rotation of flexible shafts 61a, 61b and 61c (FIG. 5) as the ratchet type handle 44 is rotated around the axis of the rotary shaft 63, thereby to clamp and unclamp the surface to be examined.

Figure 8A:
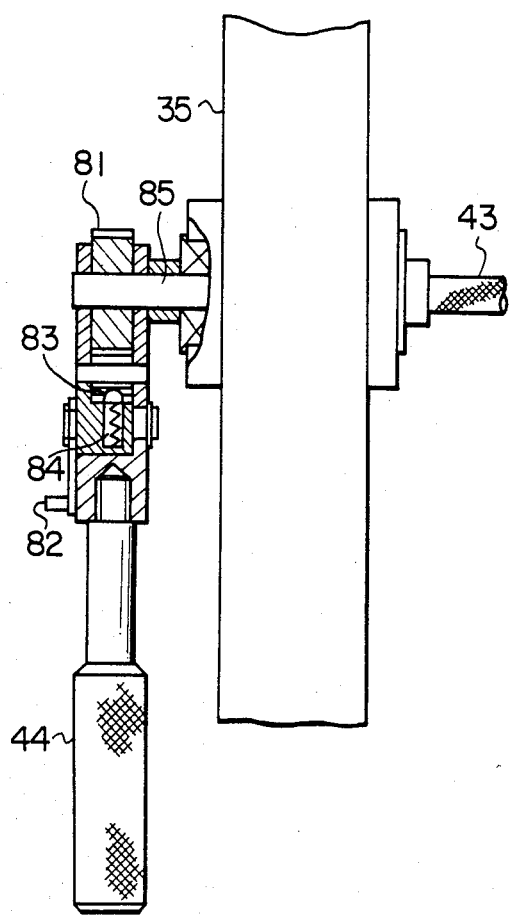
FIG. 8A is a partly-sectioned enlarged view of a portion of a handle portion.
Figure 8B:
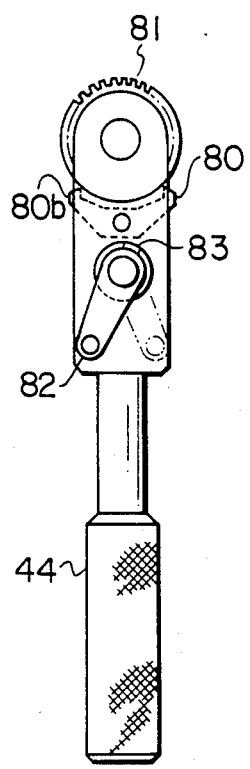
FIG. 8B is a side elevational view of the handle portion.

As the handle 44 is reciprocated, as shown in FIGS. 8A and 8B, the gear 81 is rotated only in one direction through the ratchet 80 so that the shaft 85 is rotated to rotate the flexible shafts 61a, 61b, 61c (FIG. 5) in the holder 35 to thereby project or retract the movable claws 60a, 60b, 60c. Namely, torque is transmitted from the shaft 85 to the flexible shaft 43 connected to the guide rail 34 to simultaneously project or retract the movable claws 100a, 100b, 100c (FIG. 11) adjacent to the guide rail 34. For releasing, the handle 82 is swung in the reverse direction to change the position at which the pin 83 presses the ratchet 80 to thereby press another ratchet 80b to the gear 81 thereby enabling the shaft 85 to be turned in reverse.

The transmission mechanism in the holder 35 includes, as shown in FIG. 9, a bevel gear 88 driven by the shaft 85, with the bevel gear 88 driving shafts 86a and 86b through bevel gears 87a and 87b. Furthermore, the rotation of the shaft 85 is transmitted to the flexible shafts 61a, 61b connected to the couplings 90a, 90b, so that rotation is imparted to the mechanism for projecting and retracting the movable claws 60a, 60b and 60c shown in FIG. 5.

For driving the movable claws 60a, 60b, 60c as shown in FIG. 10, a flexible shaft 61c is adapted to rotate a screw 91 through a coupling 90c, thereby to move a nut 92 to change the angle of the arm 93 connected to the nut 92. Consequently, the movable claw 60c connected to the arm 93 is projected and retracted. The movable claw 60c is provided with a flexible joint 94 which can be deformed freely in accordance with the form of the surface to be examined to thereby optimumly orientate a claw portion 95 which is provided with an anti-slip rubber portion 96. The mechanisms for driving the other movable claws 60a, 60b are materially identical to that for the movable claw 60c. As shown most clearly in FIGS. 11-13, the guide rail 34 is formed as a split-type ring member consisting of two segments 35a, 35b is openable around a hinge 52 as in the case of the holder 35. Clamping and unclamping action of the guide rail 34 is accomplished are made by manipulation of a handle 41 by the same mechanism as that shown in FIG. 6. The hinge 52, however, is different from the hinge 39 of that holder 35 in the as shown in FIGS. 12A and 12B, semi-circular guide rail segments 35a and 35b are connected to each other by the hinge 52 to form a circle. For varying the angle of the guide rail segments 35a, 35b, these segments are swung around the hinge 52 along the slide surfaces 107 and 108 to clamp and unclamp the object to be examined. In this case, the pin 105, fixed to the guide rail segment 35b, slides along the hole 106 so that the angle of the sliding movement is limited by the length of the hole 106. For detaching the guide rail 34 and the holder 35 from the elbow pipe 30, the rib 49 is detached from the holder 48 after removing the driving unit 32 from the guide rail 34, and the universal joint is rotated to the starting position and fixed at a position between the leaf springs 50. Subsequently, the handles 40 and 41 are manipulated to open the holder 35 and the guide rail 34 by swinging respective segments 35a, 35b around their hinges 39 and 52. For securing the holder 35 and the guide rail 34 to the elbow pipe 30, the holder 35 and the guide rail 34 are opened by swinging their segments 35a, 35b around respective hinges 39, 52 and are secured to the external surface of the elbow pipe 30 and then the handles 40 and 41 are manipulated to close the segments 35a, 35b into ring-like form. Thereafter, the hook 46 on the end of the rib 49 is retained by the holder 48. The length of the rib 49 is beforehand adjusted optimumly by means of a turn buckle consisting of a threaded portion 53 and nut 45. Then, the handle 44 shown in FIG. 3 is manipulated to drive the movable claws 60a, 60b, 60c and 100a, 100b, 100c of the holder 35 and the guide rail 34 to thereby clamp the elbow pipe 30. Finally, the driving unit 32 is mounted on the guide rail 34.

Figure 13:
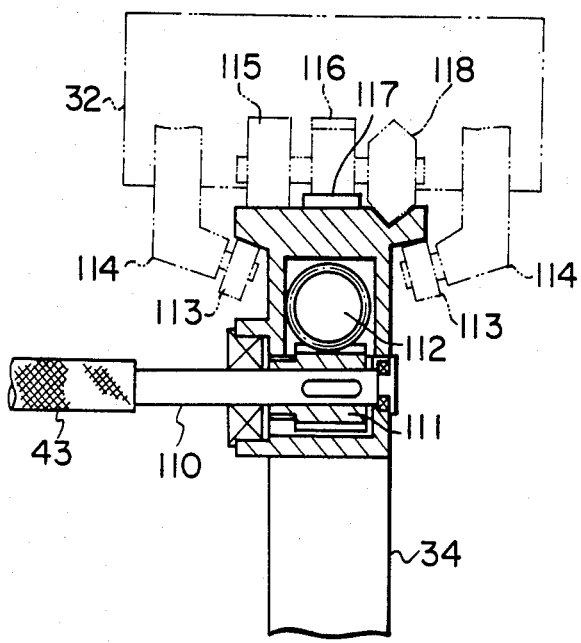
FIG. 13 is a partly-sectioned enlarged view of a torque transmitting mechanism.

FIG. 13 shows the detail of the rotary shaft 101. The torque transmitted from the holder 34 through the flexible shaft 43 is then transmitted to a screw gear 112 through a shaft 110 and a screw gear 112 thereby to rotate the flexible shaft operatively connected to the movable claw. The driving unit 32 is secured to the guide rail 34 by means of rollers 113 on the arms 114. At the same time, the driving power from the rollers 115, 118 and motor (not shown) is transmitted to the pinion 116 meshing with the rack 117 so that the driving unit 32 runs along the guide rail 34. During running, the driving unit 32 is safely carried by the rollers 113, 115 and 118, and is prevented by the roller 118 from being offset laterally.

Figure 14:
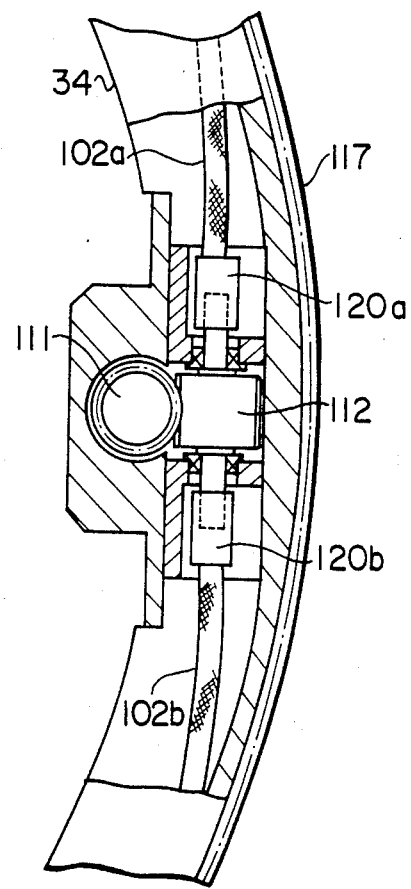
FIG. 14 is a partly-sectioned side elevational view of the portion shown in FIG. 13.

The torque from the holder 34 is transmitted to the shaft 110 and screw gears 111, 112 through the flexible shaft 43. As shown in FIG. 14 the torque of the screws 111 and 112 is transmitted to the couplings 120a, 120b and the flexible shafts 102a, 102b and drives the right and left-hand screw similar to that shown in FIG. 10 thereby to project and retract the movable claws 100a, 100b, 100c to clamp and unclamp the object to be examined.

Figure 11:
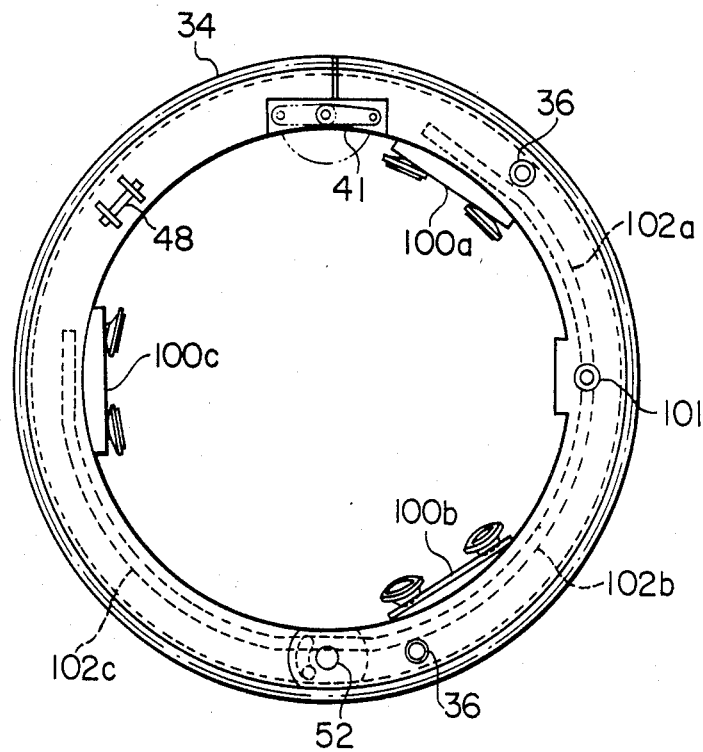
FIG. 11 is a front elevational view of the whole part of guide rail.
Figure 12A:
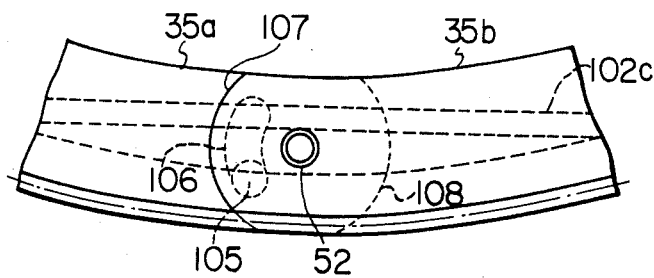
FIG. 12A is an enlarged view of the hinge portion of the guide rail.
Figure 12B:
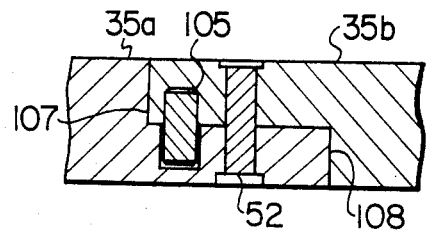
FIG. 12B is a sectional view of the central part of the portion shown in FIG. 12A.

The movable claws 100b shown in FIG. 11 is secured at a certain inclination due to the curvature of the outer surface of the elbow pipe, in contrast to the other movable claws 100a and 100c. Then, the driving unit 32 secured to the outer periphery of the guide rail 34 is held by the rollers 113 connected to the arms 114 and the rollers 115, 118 contacting the outer surface, and is driven by the mutual engagement between the pinion and the rack 117. In this case, since the roller 118 is received by the V-shaped groove formed in the outer surface of the guide rail 34, the driving unit 32 is located in the direction perpendicular to the circumference of the guide rail 34.

As has been described, according to the invention, there is provided a guide rail apparatus applicable even to pipes having complicated form such as elbows, so that the applicability of the automatic flaw detection or the like is remarkably widened and the rate of adoption of automatic control can be increased as compared with the prior art. In addition, since the guide rail 34 is mounted to extend in parallel with the weld line 31, the movement of the probe 33 achieved by the driving unit 32 can be advantageously simplified. This arrangement, therefore, offers various advantages such as reduction of number of drive shafts in the driving unit 32, simplification of the mechanism and reduction in number of the probe 33. The number of position signals and angle signals is also decreased to facilitate the processing of signals. Furthermore, since the mounting/removing of the apparatus can be made by a simple operation, the time length required for the manipulation is very much shortened to decrease the exposure to radioactive rays. Thus, according to the invention, it is possible to achieve remarkable improvement in the aspects of adaptability to piping having complicated form, maneuverability and accuracy of examination.

Figure 15:
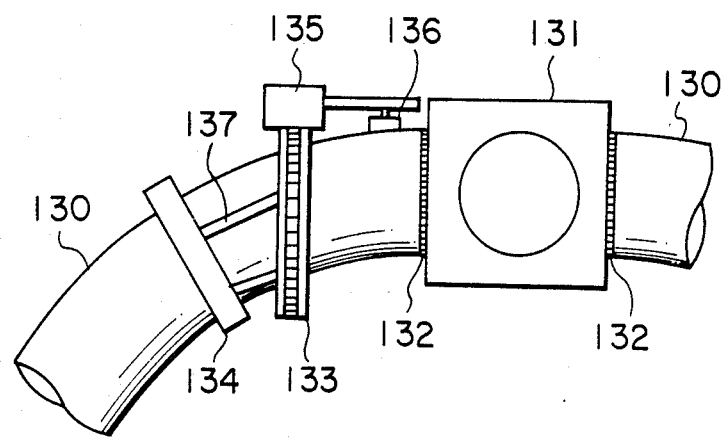
FIGS. 15 and 16 are schematic illustrations of different embodiments of the invention.

Although the above embodiment has been described on the assumption that the apparatus is applied to an elbow pipe, the apparatus of the invention can equally be applied to piping having other complicated forms such as a bent pipe as shown in FIG. 15.

In the above described embodiment, the guide rail 34 and the holder 35 are connected to each other by means of an expandable rib 36. However, the use of an expandable rib is not essential and it is possible to use a rigid rib 137 such as shown in FIG. 15.

In the above described embodiment of the invention, the movable claws 60a, 60b, 60c and 100a, 100b, 100c on both of the holder 35 and the guide rail 34 are driven by the manipulation of a single handle 44 to effect the clamping and unclamping action of both members simultaneously. This arrangement, however, is not exclusive. Namely, it is possible to arrange such that the holder 35 and the guide rail 34 are operated independently by respective handles. It is also possible to place a rubber or the like elastic member between the pipe surface and the members mounted on the pipe surface.

Furthermore, the described construction of the guide rail can be substituted by any other suitable construction.

Figure 16:
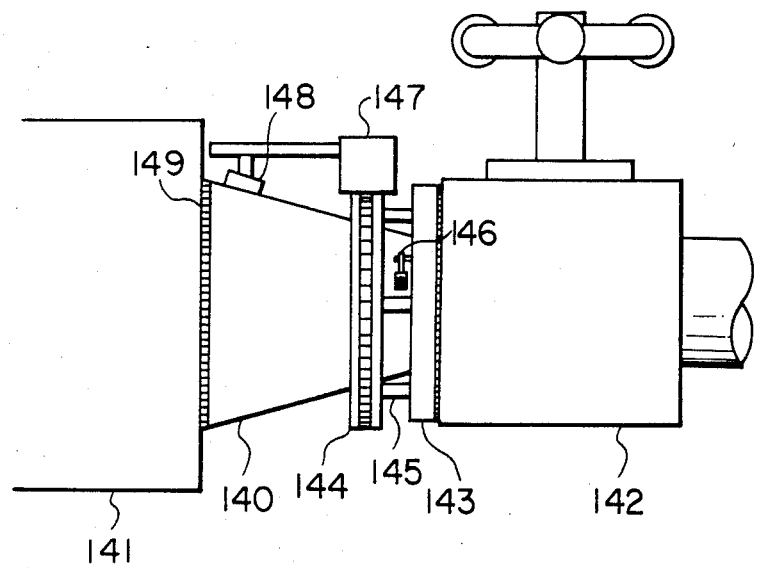
Figure 17:
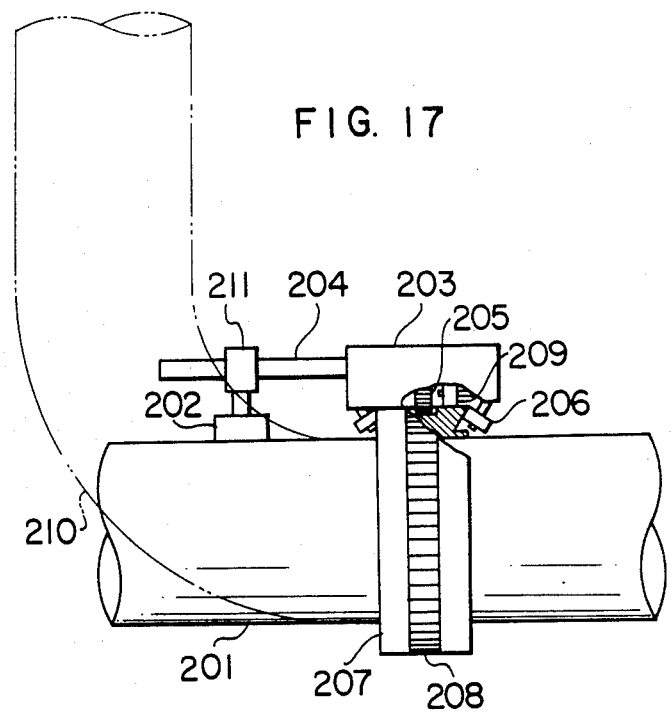
FIG. 17 is a side elevational view of a conventional apparatus for straight pipes.

In the above described embodiment, two ribs 36 are used at each side but the number of ribs 36 is not limited to two. The ring-like form of the holder 35 is not esssential and can be varied to meet the demand. Although in the described embodiment each of the holder 35 and the guide rail 34 are divided into two semi-circular segments such that the hinge and the opening diametrically oppose to each other, this is not exclusive and the angle of opening may be varied as desired provided that it permits each of the holder 35 and the guide rail 34 clear of the pipe during mounting and removal. In other words, the angular distance between the hinge and the opening may be greater or less than 130°. For instance, as shown in FIG. 16 in the examination of a reducer pipe 140 between the valve 143 and a pump 141, a holder 143 is secured to the portion near the juncture between the reducer pipe 140 and the valve 142 so that the guide rail 144 can be fixed more securely than the case where the guide rail 144 is disposed at the inclined portion. It is thus possible to secure a driving unit 147 even to such a pipe The guide rail apparatus can be broadly used as guide rail apparatur for various types of automatic apparatus such as automatic welder, industrial robot or the like.

Figure 18:
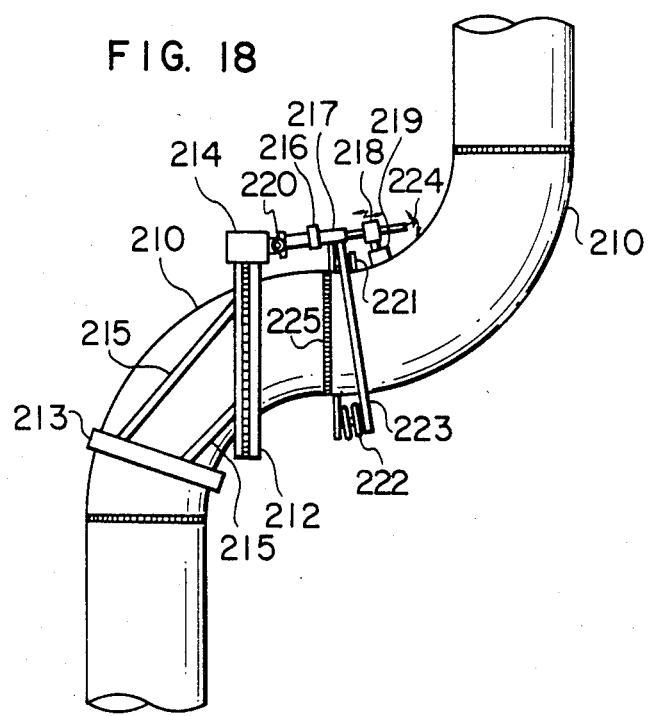
FIGS. 18 and 19 are side elevational views of an apparatus in accordance with the invention attached to an elbow pipe.

FIG. 18 shows another embodiment of the invention wherein a driving unit 214 is mounted on a rail 212 secured to a piping 210 consisting of two elbows welded to each other. The axial scanning movement of the probe 219 is effected by means of a motor mounted on a truck 216 which moves on an arm 217 through a screw while transmitting the torque of the motor to a screw extending in parallel with the arm 224 to shift a holder 218. A mechanism is provided for making the probe 219 move following up the form of the surface of the piping 210 and the angle between the arms 217 and 224 around the shaft 220 is varied around the shaft 220. The circumferential scanning by the probe 219 is effected by means of the driving unit 214 which is adapted to move along the outer surface of the track 212 secured by means of a holder 213 through ribs 215.

Figure 19:
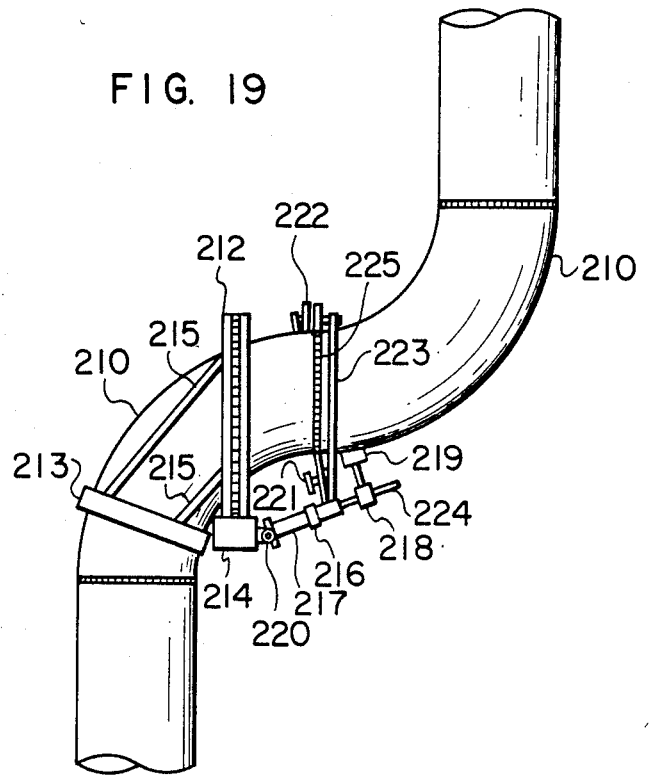

More specifically, the driving unit 214 has a motor the output torque of which is transmitted to a pinion meshing with a rack on the rail 212 so that the driving unit as a whole runs along the track 212. The rollers 221 and 222 provided on the arms 223 are kept in contact with or away from the pipe surface depending on the shape of the latter to vary the angle of the arm 217 and the arm 224. For instance, as the driving unit 214 is moved to the lower part of the rail 212 as shown in FIG. 19, the arms 217 and 224 are lowered around the shaft 220 by the force of gravity, so that the driving unit 214 is held by rollers 222 provided on the ends of the arms 223 extending around the pipe 210.

Figure 20:
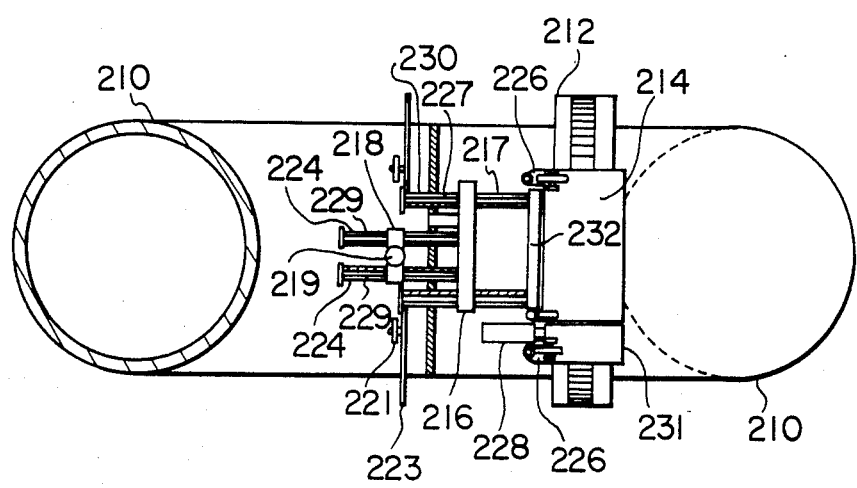
FIG. 20 is a plan view of the apparatus shown in FIGS. 18 and 19.

As shown in FIG. 20, the driving unit 214 has a circumferential driving section 231 for the driving in the circumferential direction. In order to cope with the change in the outside diameter of the rail 212, various angles in the driving unit 214 are changeable. The mounting of the driving unit 214 on the rail 212 is made by the mounting/removal mechanism 226 basically same as that shown in Japanese Patent Application No. 92939/1978. The detail of this mechanism will be described later. In order to avoid interference with the piping 210 such as elbow, the mounting/removal mechanism 226 and the motor 228 are projected in the same side as the arm 217. On the other hand, the axial driving is made by driving the truck 216 along the arm 217 by rotating a nut meshing with the screw 230 by means of the motor 227. At the same time, the rotation of the motor 207 is transmitted also to a screw 229, so that the holder 218 with the probe 219 is moved along the arm 224. Consequently, the movement of the probe 219 is doubled by the truck 216 and by the holder 218.

Figure 21:
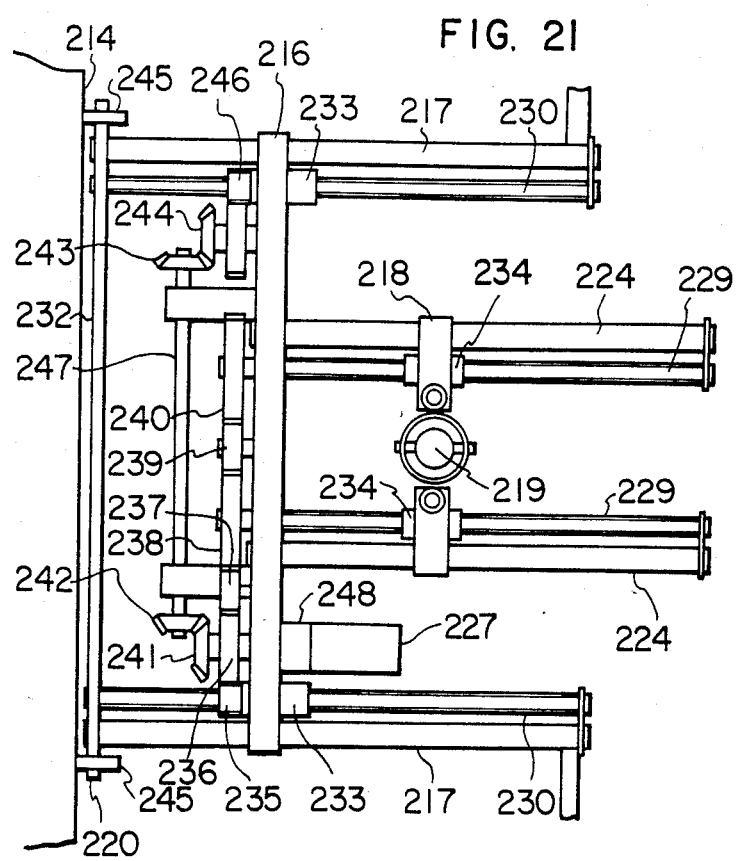
FIG. 21 is a plan view of an expandable arm.

The axial driving section is mounted on the track 232 which is mounted to freely change the angle between the driving unit 214 and the arms 217, 224. At the same time, an arm 223 is secured to the end of the arm 217. In the power transmission mechanism in the axial driving section, as shown in FIG. 21, the torque of the motor 227 is transmitted from a gear 236 to a gear 235 through a speed reducer 248 to thereby drive the nut 233 and, at the same time, a gear 246 is rotated through gears 241, 242, shaft 247 and gears 243, 244 to thereby drive another nut 233. Consequently, the nuts 233 are moved upon engagement with the screws 230 to drive the truck 216 along the arm 217. On the other hand, the rotation of the gear 236 is transmitted through a gear 237 to gears 238, 239 and 240. Consequently, two screws 229 are rotated to drive the nut 234 integral with the holder 218. As a result, the speed of movement of the probe 219 is doubled because the probe 219 moves along the arm 224 while the truck 216 moves along the arm 217.

This axial driving section is secured to the truck 232 and also secured by the holder 245 of the driving unit 214. Namely, the axial driving section is held rotatably by a shaft 220 received by a hole formed in the holder 245.

Figure 22:
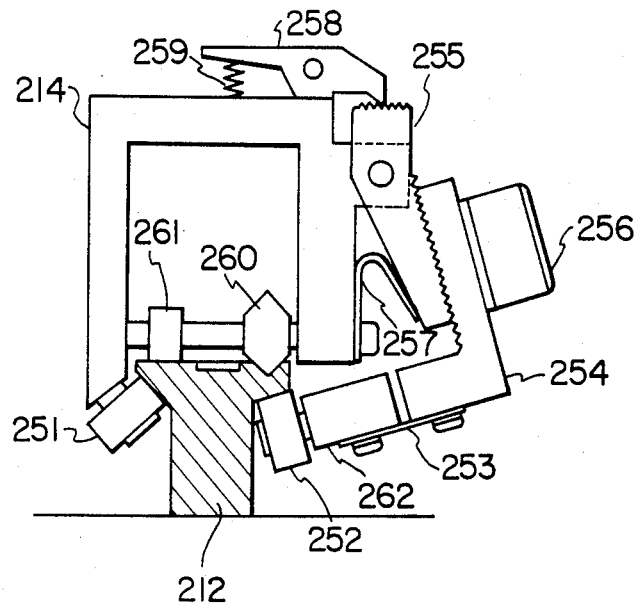
FIG. 22 is a side elevational view of a mounting-/demounting mechanism.

In the mounting/removing mechanism 226, as shown in FIG. 22, the driving unit 214 is held by means of rollers 251, 252 contacting with the inclined portion of the rail 212. For disengaging one 252 of the rollers, a ratchet 258 is pressed to disengage the claw on the end of the ratchet 258 from the teeth of the arm 255, so that the arm 254 as a unit with the leaf spring 253 and the holder 262 is swung outwardly to open to thereby permit the removal of the driving unit 214. For mounting the driving unit, the arm 254 is pressed so that the claw on the end of the ratchet 258 successively move on the teeth of the arm 255 by the action of the spring 259 to thereby press the roller 252 onto the inclined surface of the rail 212. The joint surfaces of the arm 254 and the arm 255 are provided with complementary projections and recesses meshing with each other, and the two arms 254 and 255 are fastened in this state to each other by means of a screw 256. The length is adjusted in accordance with the change by means of the screw 256 in accordance with the change in the diameter of the rail 212. The outer peripheral surface of the rail 212 has a V-shaped groove and flat surfaces. Two pairs of V-shaped rollers 260 and 261 make rolling contact with this outer peripheral surface to thereby axially locate the driving unit 214.

Figure 23:
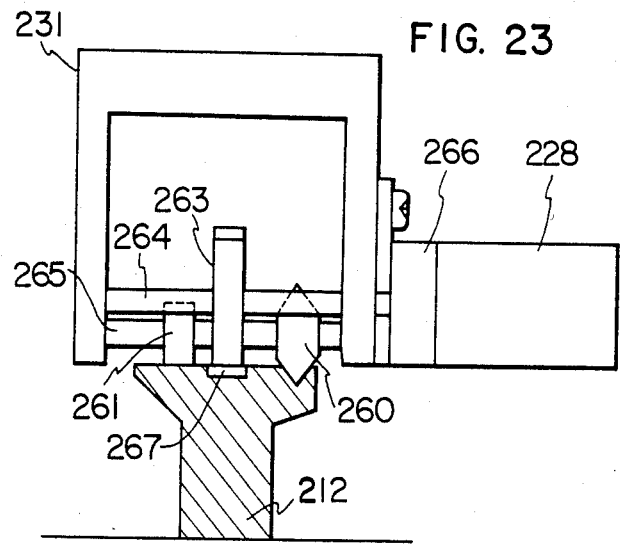
FIG. 23 is a side elevational view of a circumferential driving unit.

In the circumferential driving section, as shown in FIG. 23, the torque of the motor 228 is transmitted from the motor 228 to the pinion 263 through the speed reducer 266, so that the circumferential driving section is moved circumferentially through the mutual engagement between the rack 267 of the rail 212 and the pinion 263. Two sets of V-shaped rollers 260 and 261 located at another position serve to adjust the condition of meshing between the pinion 263 and the rack 267.

Figure 24:
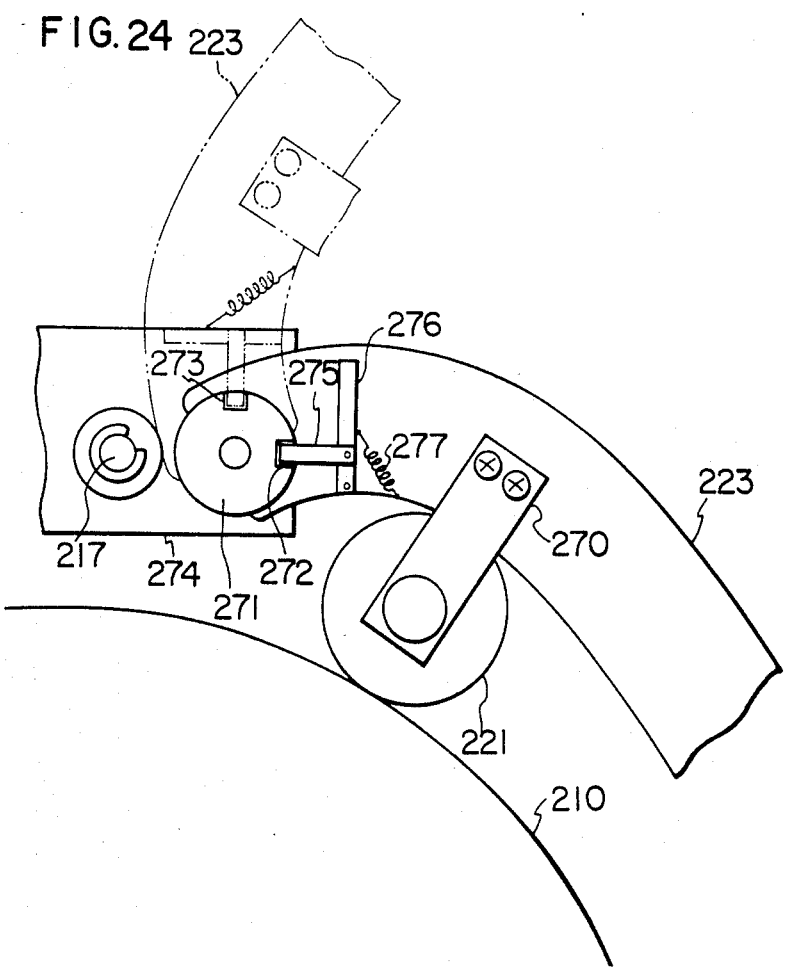
FIG. 24 is a side elevational view of a mechanism for holding the expandable arm.
Figure 25:
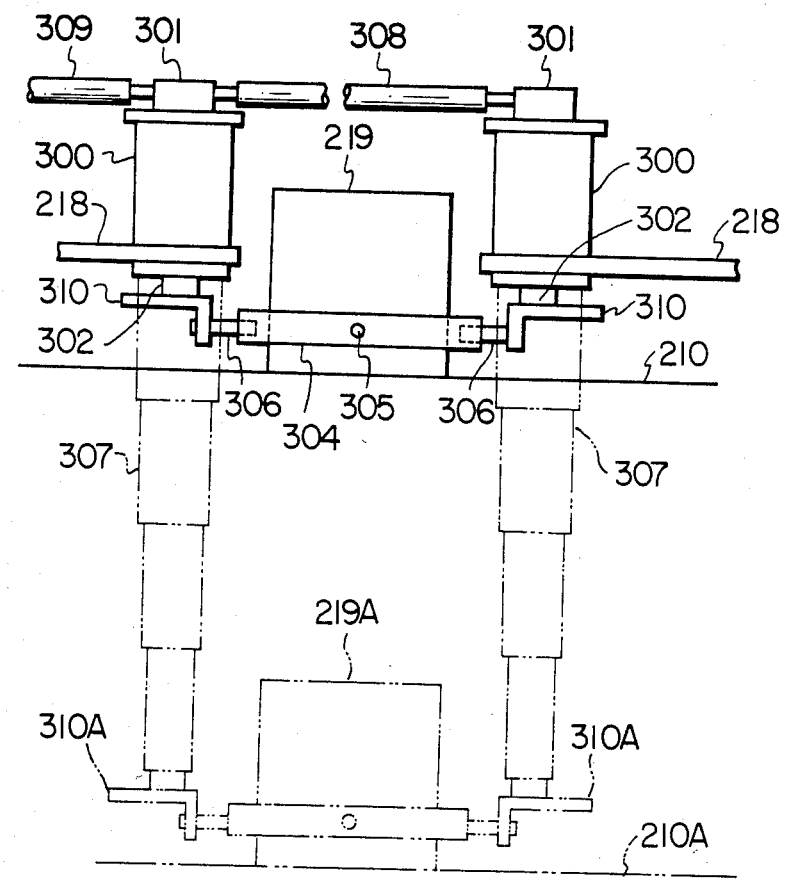
FIGS. 25 and 26 shows side elevational views of a probe pressing mechanism.
Figure 26:
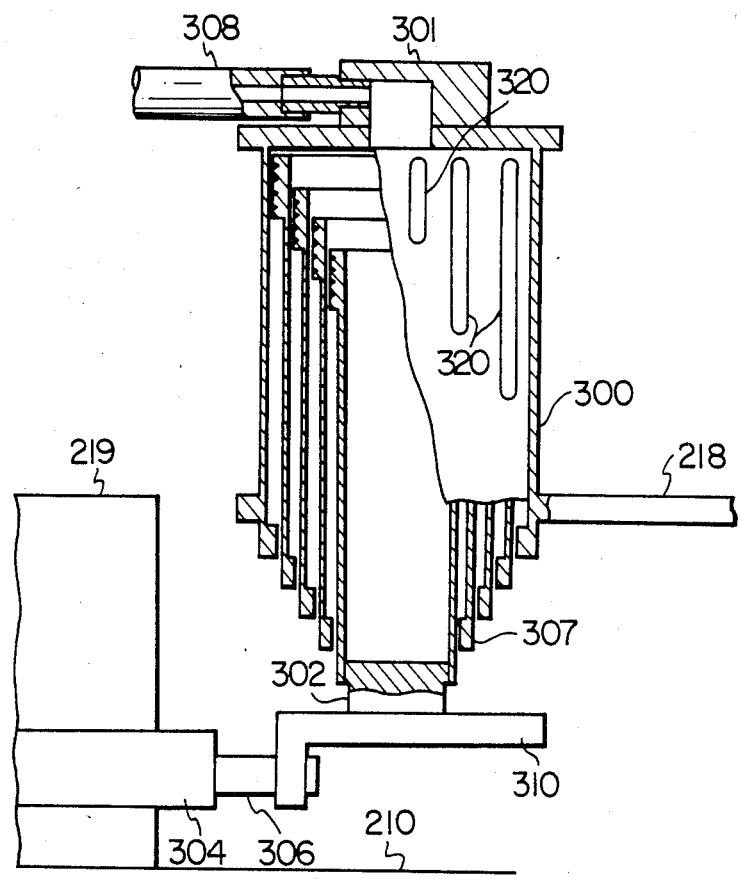

For opening the arm 223 to permit the removal, as shown in FIG. 24, a shaft 275 inserted into a groove 272 of a stopper 271 formed on the rotary shaft of the arm 223, is withdrawn from the same by a mainipulation of a lever 276 to permit the arm 223 to rotate and, then, the shaft 275 is inserted into aother groove 273, so that the arm 223 is fixed at the opening position. The closing of the arm 223 is made in the same manner by inserting the shaft 275 into the groove 272. As shown in FIG. 25, in order to follow up the surface of the piping 210, the probe 219 is adapted to rotate around the axis of a shaft 305 interconnecting a ring 304 and the probe 219 until the ring 304 comes to interfere the probe 219. At the same time, the probe 219 is connected to the ring 304 by means of a shaft 306 provided on the holder 310, to permit a rotation in the direction which is 90° offset from the direction of the shaft 305. A pneumatic cylinder 300, which is secured to the holder 218 through a shaft 302, is adapted to press the probe 219 resiliently against the surface of the piping 210. The penumatic cylinder 300 is supplied with air of a predetermined pressure from air tubes 309, 308 through an air supply port 301. Consequently, as the surface to be examined is varied as in the case of the pipe 210A, the inner cylinder or plunger 307 of the pneumatic cylinder 300 is pressed by the air to resiliently press the probe 219A against the pipe surface following up the curvature of the same. As shown in FIG. 26, the pneumatic cylinder 300 accomodates a plurality of inner sleeves 307 which are housed completely by the pneumatic cylinder 300 when the latter is in a contracted condition. Then, as the condition of the surface of the piping 210 is changed, the inner sleeve 307 of the smallest diameter and, then, the inner sleeve of diameter next to the smallest and so forth are successively extended by the pressure of air supplied into the pneumatic cylinder 300 through the pneumatic tube 308 and the air supplying port 301 to follow up the change in the condition of the pipe surface. The inner sleeves 307 are forced into the pneumatic cylinder 300 in the following cases, namely, where the force is applied solely by the weight of members such as arm 217, arm 224, arm 223 and so forth as shown in FIG. 18, and where the condition of surface of the pipe 210 in relation to the movement of the driving unit 214 around the fulcrum constituted by the roller 222 of the arm 223. In this case, the force required for contracting the inner sleeves 307 is increased as the diameter of the inner sleeves 307 becomes greater to increase the reactional force against the contracting force. To avoid this, it is quite effective to form grooves 320 in the inner peripheral surfaces of the pneumatic cylinder 300 and the inner sleeve 307 to permit the leakage of air in accordance with the stroke to thereby decrease the reactional force. By constructing the pneumatic cylinder 300 to operate in a plurality of stages as, it is possible to obtain a long stroke while diminishing the size of the pneumatic cylinder in the contracted condition. Additionally, since a force perpendicular to the holder 310 can be applied, the scanning operation of the probe 219 on the pipe surface is very stabilized, and, the pressing force becomes more free from the influence of the stroke due to the adjustment permitted by the air relieving grooves 320.

According to this embodiment of the invention, it becomes possible to conduct an automatic flaw detection on the pipe surface having a complicated shape, e.g. the weld joint between two elbows. Additionally, the length of time required for the flaw detection can be shortened remarkably because the scanning speed of the probe is doubled. Furthermore, the running is stabilized and the precision of position is enhanced because the screws 229, 230 and the arms 217, 224 are disposed at both sides. Furthermore, since the driving section is disposed in the circumferential direction and since the arms 17 and 24 are made to open at their ends, the interference of these arms with the probe 219 is suppressed as compared with the prior art in which the holder plate is provided at the end. Consequently, it is possible to reduce the height from the pipe surface.

To sum up, the last described embodiment offers the following advantages.

Since the apparatus is adaptable to piping having complicated form, the ratio of automation is very much increased. Namely, it is possible to vary the arm angle and arm length in accordance with the complicated form of the piping, and to control the pressing stroke and the pressing angle following up the change in the condition of the pipe surface. For instance, in the case where the pipe to be examined consists of elbows welded to each other, it is possible not only to effect the scanning following up the form of the pipe but also to effect such an automatic adjustment as to reduce the stroke on the portion of the elbow of small curvature to prevent the interference of the arm end while, on the portion of the elbow having a large curvature, the stroke is increased to a sufficiently large length.

Furthermore, height from the pipe surface can be decreased by the angle of axial arms 217, 224. Consequently, the interference with the structure around the pipe is diminished to further contribute to the increase of adaptability of the apparatus. Additionally, since the arm angle can be varied following up the change in the form of the pipe, it is not always necessary to arrange the rail concentrically with the pipe, which also serves to reduce the height from the pipe surface. For instance, in the case where the pipe consists of an elbow and a straight pipe connected to each other, it is necessary that the rail has a large diameter due to the presence of small-curvature portion in the elbow, if the rail has to be installed concentrically with the straight pipe, resulting in a large height from the pipe surface. This, however, can be avoided by arranging the rail at a certain eccentricity from the straight pipe.

Furthermore, the axial arm is extended, the running object can be retracted to the original position of the arm 217 and can be pushed forward to the position of the end of the arm 224. Consequently, it is possible to increase the length of the arm or the ratio of the effective stroke to the overall length of the apparatus, which in turn permits a reduction in the length of the apparatus. Furthermore, when there is an obstruction such as valve on the end of the pipe or when the examination is effected on the inward curvature of the elbow-elbow piping, it is possible to select beforehand the length in such a manner as to avoid interference with the arm 224. Thus, the apparatus of the invention can be used with a large flexibility or adaptability to a large variety of condition around the piping.

Also since the torque is transmitted simultaneously from a single motor 227 to the nut 233 and the screw 229, it is possible to double the running speed of the running body. If there is any margin in the running speed of running body per revolution of the motor shaft, it is possible to increase the driving torque by reducing the running speed by an amount corresponding to the margin. It is thus possible to obtain either a higher speed or a greater torque depending on the purpose or use.

Moreover, in the case where the axial scanning is limited by an obstruction residing in the lengthwise direction of the pipe, it is possible to arrange such that the torque of the motor 27 is transmitted solely to the screw 229, so that only the truck 218 is driven without causing any stretching of the arm 224.

Moreover by forming air relieving grooves in the inner sleeves of the pneumatic cylinder, it is possible to make the probe follow up the change in the form of the pipe surface simply by supplying air only to one side of the cylinder. Additionally, it is possible to remarkably decrease the size of the cylinder by constructing the same to perform extension and retraction in a plurality of stages. This arrangement also ensures, in combination with the zinbal mechanism, a high fidelity of the running body to large change in the form of the examined surface.

In the last described embodiment, the arm is adapted to be extended and retracted in two stages. This, however, is not exclusive and it is possible to obtain a four-stage operation by adding the same combination of the motor, nut and the screw and applying an equal voltage to both motors. Thus, the number of stages of the expandable arm is not limited and can be varied as desired.

Although in the described embodiment the angle of the expandable arm can be varied as desired, the expandable arm may be used at a fixed angle in the examination of a pipe having a simple configuration such as a straight pipe.

Furthermore, the expandable arm which is located at each side of the probe in the described embodiment, may be provided only at one side of the probe if there is no sufficient room for mounting the arm or when the requirement of the precision of position is not so severe. By omitting the expandable arm at one side of the probe, the construction of the whole apparatus can be simplified remarkably.

Also, although in the last described embodiment the expandable arm is opened at its one end and cantilevered to reduce the height from the pipe surface, it is possible to connect the ends of two arms of the same stage in some uses.

Figure 27:
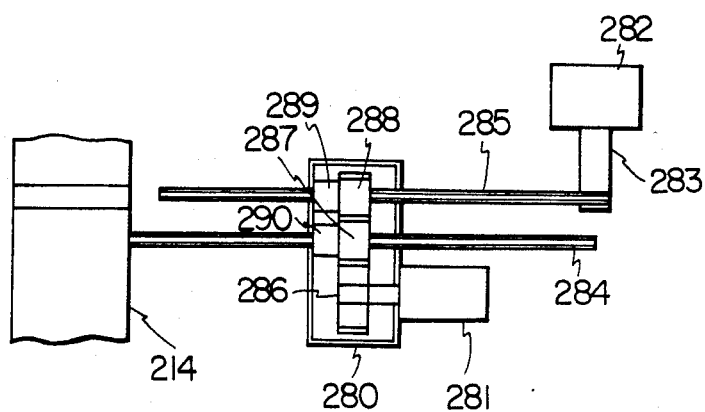
FIG. 27 is an illustration of operation of another expandable arm.

FIG. 27 shows a modification of the expandable arm, and according to this figure, the torque of the motor 281 is transmitted to gears 287, 288 through a gear 286 to thereby rotate the nuts 290 and 289 meshing with the screws 284 and 285. By so doing, the truck 280 is moved along the screw 284 and, at the same time, the screw 285 is moved, so that the probe attached to the holder 285 on the end of the screw 285 can be moved at a doubled speed for scanning.

Figure 28:
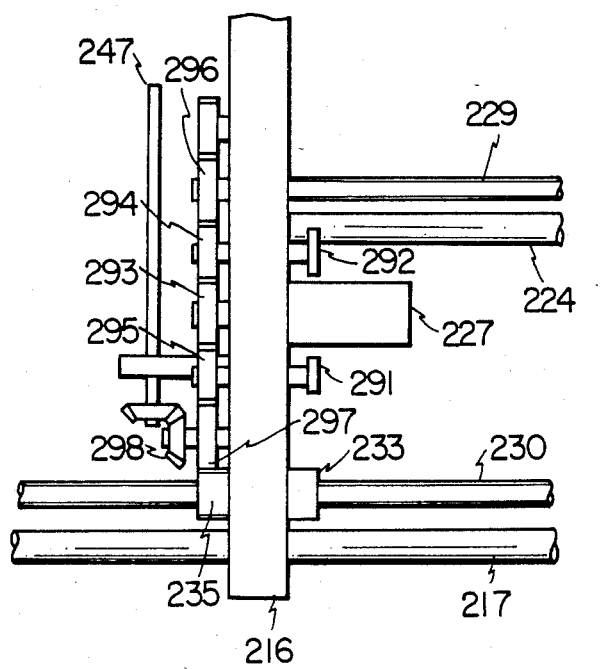
FIG. 28 is an illustration of another modification.

FIG. 28 provides an example of another embodiment for feeding two stages of arm simultaneously more particularly, in in FIG. 28, the torque of the motor 227 can be changed as desired by means of buttons 291, 292 and gears 294 and 295 are switched as desired to drive the screw 229 solely or the nut 233 solely. For instance, in the case where the arm cannot be sufficiently stretched due to the presence of an obstruction, the gear 295 is disengaged to permit the screw 229 solely, so that the arm is not elongated because the truck 216 does not move. In such a case, the probe moves only along the arm 224 and the screw 229.

In the arrangement shown in FIG. 20, there are provided three sets of mounting/removal mechanisms 226. However, the mechanism 226 may be provided in duplicate for each driving section. Namely, the number of the mechanisms 226 may be increased or decreased depending on the uses and the shape and the position of the mechanisms may be selected freely. It is also possible to mount the roller 251 for free adjustment of angle, although it is fixed in the arrangement shown in FIG. 22.

It is also possible to substitute the air relieving grooves in the inner surfaces of multi-staged pneumatic cylinder by valves or the like which automatically regulate or control the pneumatic pressure in the pneumatic cylinder which gradually increases in response to the reactional force from the probe or the like. The described multi-staged pneumatic cylinder can be used as an independent device for automatic flaw detector for other purposes or even to other applications.

Althouth the invention has been described through specific forms applied to the examination of pipes having elbows, the described embodiments are only for the illustrative purpose and the invention can be applied, needless to say, to the guiding of running object around other bent pipes and straight pipes. Although no specific description has been made as to the means for detecting the positions and angles of the drive shafts, it will be clear to those skilled in the art that the apparatus of the invention incorporates means for obtaining such information.

What is claimed is:

1. A guide rail apparatus for guiding a running body along an outer peripheral surface of a piping, the apparatus comprising a guide rail including two segments adapted to fit around said piping; a holder including two segments fitting around said piping, said holder being spaced in an axial direction from said guide rail, openable ends of said segments of said guide rail and said holder are located at the same side as said piping; and a rigid connector means for integrally connecting said guide rail and said holder to each other.

2. A guide rail apparatus as claimed in claim 1, wherein each of said guide rail and said holders is provided with a pipe clamping means, said pipe clamping means of said guide rail and said pipe clamping means of said holder being connected to each other by a flexible shaft, and wherein at least one of said guide rail and said holder is provided with a handle means for actuating said pipe clamping means through said flexible shaft.

3. A driving apparatus for an ultrasonic probe comprising: circumferential driving means for driving said probe in a circumferential direction of a pipe to be examined, means on said circumferential driving means for moving said probe in an axial direction of said pipe; connecting means for connecting said means for moving to said circumferential driving means at a varying angle; and an expandable means provided on said means for moving for pressing said ultrasonic probe on said pipe to be examined.

4. A guide rail apparatus for guiding a running body running around a pipeing, the apparatus including a circumferential driving means for driving an ultrasonic probe in a circumferential direction of the piping to be examined, means on said circumferential driving means for moving said probe in an axial direction of said piping, connecting means for connecting said means for moving and said circumferential driving means at a varying angle, an independent expandable means on said means for moving for pressing said ultrasonic probe onto said piping, a guide rail apparatus for guiding the running body along an outer peripheral surface of the pipeing, including a guide rail comprising two segments adapted to fit around said piping; a holer comprising two segments fitting around said piping, said holder being spaced in an axial direction from said guide rail, with openable ends of said segments of said guide rail and said holder being located at the same side of said piping; and a rigid connector means for integrally connecting said guide rail and said holder to each other.

* * * * *